United States Patent [19]

Fruchey et al.

[11] Patent Number: 5,120,855
[45] Date of Patent: Jun. 9, 1992

[54] FORMATION OF HYDROXYAROMATIC KETOACETAL FROM A HYDROXYAROMATIC METHYLKETONE AND PRODUCTION OF 5-(4'-HYDROXYPHENYL)HYDANTOIN AND DP-HYDROXYPHENYLGLYCINE FROM 4-HYDROXYACETOPHENONE

[75] Inventors: Olan S. Fruchey, Bad Soden T. S., Fed. Rep. of Germany; Graham N. Mott; John R. Durrwachter, both of Corpus Christi, Tex.

[73] Assignee: Hoechst Celanese Corporation, Somerville, N.J.

[21] Appl. No.: 628,238

[22] Filed: Dec. 13, 1990

Related U.S. Application Data

[63] Continuation-in-part of Ser. No. 451,675, Dec. 14, 1989, abandoned.

[51] Int. Cl.⁵ .......................................... C07D 233/78
[52] U.S. Cl. .................................... 548/313; 568/315; 568/337; 568/442; 562/444
[58] Field of Search ............... 548/315; 562/444; 568/315, 337, 442

[56] References Cited

U.S. PATENT DOCUMENTS

| | | | |
|---|---|---|---|
| 4,094,741 | 6/1978 | Yamada et al. | 435/129 |
| 4,230,869 | 10/1980 | Yoneda et al. | 548/314 |
| 4,436,910 | 3/1984 | Kleemann et al. | 546/245 |

FOREIGN PATENT DOCUMENTS 53-112874 10/1978 Japan .

OTHER PUBLICATIONS

"Advances in Heterocyclic Chemistry", edited by Alan R. Katritzky, Academic Press, Inc., vol. 38, 1985, pp. 177-228.
"The Chemistry of Hydantoins", Elinor Ware, Chem. Rev. 46, 1950, pp. 403-470.
"Microbial Production of D-p-Hydroxyphenylglycine", S. Takahashi, Prog. Ind. Microbiol. 24(Biotechnol. Amino Acid Prod.), 1986, pp. 269-79.
"Production and Utilization of Amino Acids", Yoshihara Izummi et al., Angew. Chem. Int. Ed. Engl. 17, 1978, pp. 176-183.
Noller, Carl "Chemistry of Organic Compounds", (1965) W. B. Saunder Co. Philadelphia, pp. 243, and 844.
Yamada et al., Agric. Biol. Chem., 43 (2), 395-396 (1979).

Primary Examiner—Marianne Cintins
Assistant Examiner—John Peabody
Attorney, Agent, or Firm—Donald R. Cassady; Stuart D. Frenkel

[57] ABSTRACT

The present invention provides a method for producing a hydroxyaromatic ketoacetal from a hydroxyaromatic methylketone. The invention further provides a method for producing a hydroxyaromatic ketoaldehyde from a hydroxyaromatic ketoacetal. The hydroxyaromatic ketoaldehyde can be further reacted to form a hydantoin, which hydantoin can be hydrolyzed to produce a hydroxyphenylglycine.

59 Claims, No Drawings

FORMATION OF HYDROXYAROMATIC KETOACETAL FROM A HYDROXYAROMATIC METHYLKETONE AND PRODUCTION OF 5-(4'-HYDROXYPHENYL)HYDANTOIN AND DP-HYDROXYPHENYLGLYCINE FROM 4-HYDROXYACETOPHENONE

CROSS REFERENCE TO RELATED APPLICATION

This application is a continuation-in-part of U.S. patent application Ser. No. 07/451,675 filed Dec. 14, 1989 now abandoned which is incorporated herein by reference.

BACKGROUND OF THE INVENTION

The present invention pertains to the formation of an hydroxyaromatic ketoacetal from an hydroxyaromatic methylketone, to the formation of hydroxyaromatic ketoaldehyde from an hydroxyaromatic ketoacetal, and further to the formation of an hydantoin from the hydroxyaromatic ketoaldehyde. The invention also pertains to subsequent hydrolysis of the hydantoin to produce a hydroxyphenylglycine, and to techniques for resolution of optical isomers to provide a D-hydroxyphenylglycine.

In particular, the present invention relates to an improved process for the production of hydantoins and glycines. More particularly, the invention relates to a process for the preparation of 5-(4'-hydroxyphenyl)-hydantoin and p-hydroxyphenylglycine, and to the resolution of D-p-hydroxyphenylglycine, wherein the starting material for production of the hydantoins is 4-hydroxyacetophenone.

5-(4'-Hydroxyphenyl)hydantoin is an important intermediate in the production of D-4-hydroxyphenylglycine which is employed for preparing semi-synthetic penicillins and cephalosporins. It is known that 5-(4'-hydroxyphenyl)-hydantoin may be synthesized by the reaction of 4-hydroxybenzaldehyde, ammonium bicarbonate and sodium cyanide according to Bucherer-Berg's method. However, this method requires the use of dangerous sodium cyanide, and further, the obtained crude hydantoin may contain large quantities of by-products caused by the oxidative side reaction of the phenol nucleus under an alkaline condition or may be colored.

U.S. Pat. No. 4,230,869 provides a process for preparing 5-(4'-hydroxyphenyl)hydantoin by reacting glyoxylic acid, urea and phenol in the presence of an acid. One disadvantage of this method is the requirement of heating to 40° to 100° to drive the reaction. 5-(4'-Hydroxyphenyl)hydantoins have also been prepared by reacting allantoin with phenol in the presence of acids as taught in Japanese Kokai 78/112874.

In the prior art, D-4-hydroxyphenylglycine has been generally prepared by chemically subjecting DL-4-hydroxyphenylglycine to optical resolution. However, such a process has the disadvantage that DL-4hydroxyphenylglycine must be converted to derivatives such as esterification and acylation products prior to subjecting it to optical resolution, or resolving reagents are required, and also process steps are required for racemizing the residual L-form.

It is also known in the art that D-4-hydroxyphenylglycine may be prepared by the enzymatic or alkali hydrolysis of 5-(4'-hydroxyphenyl)hydantoin. In this regard one may refer to Takehashi, *Microbial Production of D-p-Hydroxyphenylglycine,* Prog. Ind. Microbiol. 24(Biotechnol. Amino Acid Prod.) 269-79 (1896) and U.S. Pat. No. 4,436,510 which are incorporated herein by reference.

In U.S. Pat. No. 3,094,741, which is incorporated herein by reference, it is disclosed that DL-5-(4-hydroxyphenyl)hydantoin can be almost quantitatively converted to D-N-carbamoyl-(4-hydroxyphenyl)glycine by causing cells or treated cells of specific microorganisms to act on the hydantoin in an aqueous medium at pH 7 to 10. D-N-carbamoyl-(4-hydroxyphenyl)glycine can be converted into D-4-hydroxyphenylglycine in high yields, for instance by reacting it with an equimolar amount of nitrous acid in the presence of a strong acid.

SUMMARY OF THE INVENTION

In accordance with the method of present invention, an hydroxyaromatic methylketone is reacted to form an hydroxyaromatic ketoacetal. Also in accordance with the present invention, an hydroxyaromatic ketoacetal is reacted to form an hydroxyaromatic ketoaldehyde. Further in accordance with the present invention, the hydroxyaromatic ketoaldehyde is reacted to form a hydantoin. The hydantoin can be subsequently hydrolyzed to produce a hydroxyphenylglycine. The method of the present invention also pertains to techniques for resolution of optical isomers which techniques are combined with the reaction steps referred to above to provide a D-hydroxyphenylglycine.

More specifically, the hydroxyaromatic methylketone is reacted with a source of H+, a source of NO+, and a primary or secondary alcohol to produce the hydroxyaromatic ketoacetal. The source of NO+ can be a $C_1$ to $C_{10}$ alkyl nitrite used in combination with an acid source, such as HCl, or can be a reactant NO+X, wherein X can be halogen, sulfite, sulfate, phosphite or phosphate. Preferably X is halogen, and most preferably X is chlorine. The hydroxyaromatic ketoacetal then comprises an acetal group,

wherein R is typically $C_1$–$C_{10}$ and is a primary or secondary alkyl structure.

The hydroxyaromatic ketoacetal described above can be further reacted with water which has been previously acidified with any non-oxidizing acid to produce a hydroxyaromatic ketoaldehyde (hydroxyaromatic glyoxaldehyde).

The hydroxyaromatic ketoaldehyde can be further reacted with water, urea, and concentrated acid to produce a 5-(hydroxyphenyl)hydantoin.

Although the method of the present invention can be applied using a starting material comprising an hydroxyaromatic methyl ketone in general, the method will be specifically described in terms of a p-hydroxyacetophenone starting material. The present invention provides an improvement over known methods of preparing hydantoins and glycines. The method for preparing the hydantoins and glycines can be a one pot reaction, wherein a hydroxyaromatic methylketone such as 4-hydroxyacetophenone is contacted with a source of H+, a source of NO+, and a primary or secondary alcohol to form an intermediate, such as the dialkylacetal of 4-hydroxyphenylketoaldehyde.

The dialkylacetal of hydroxyphenylketoaldehyde, such as the dialkylacetal of 4-hydroxyphenylketoaldehyde, in the presence of water undergoes hydrolysis yielding a second intermediate, hydroxyphenylketoaldehyde, such as 4-hydroxyphenylketoaldehyde.

Without being restricted to a particular theory, it is hypothesized that the reaction proceeds as follows for conversion of 4-hydroxyacetophenone to 5-(4'-hydroxyphenyl)hydantoin.

The 4-hydroxyacetophenone (I), which is present in solution initially, undergoes acid catalyzed tautomerization to the enol form (II) in the presence of a strong mineral acid, preferably HCl. The enol then reacts with a nitrosonium ion (NO+) to form the alpha nitroso-4-hydroxyacetophenone (III). (III) undergoes an acid catalyzed tautomerization yielding alpha-oximino-4-hydroxyacetophenone (IV). The nitrosonium ion comes from an NO+ source such as nitrosyl chloride, which can be generated from the reaction of HCl with alkyl nitrite (RONO+HCl→ROH+NOCl, wherein R is $C_1$ to $C_{10}$). (IV) then undergoes a solvolysis reaction with the isopropanol solvent forming the diisopropyl acetal of 4-hydroxyphenylketoaldehyde (V). In the presence of water the acetal (V) undergoes hydrolysis yielding 4-hydroxyphenylketoaldehyde (VI) which condenses with urea to form the pinacol (VII) which in the presence of acid undergoes a pinacol rearrangement yielding the hydantoin (VIII). None of the intermediates need be isolated in the reaction, and many are only present as equilibrium mixtures which are shifted forward as the result of product formation.

In the alternative, in place of using the $C_1$ to $C_{10}$ alkyl nitrite in combination with the HCl to produce the nitrosyl chloride as described above, it is possible to use a source of NO+ directly. The source of NO+ is a reactant NO+X, wherein X can be halogen, sulfite, sulfate, phosphite, or phosphate. Preferably X is halogen, most preferably chlorine, and the source of NO+ is NOCl.

The reaction steps described above are illustrated below:

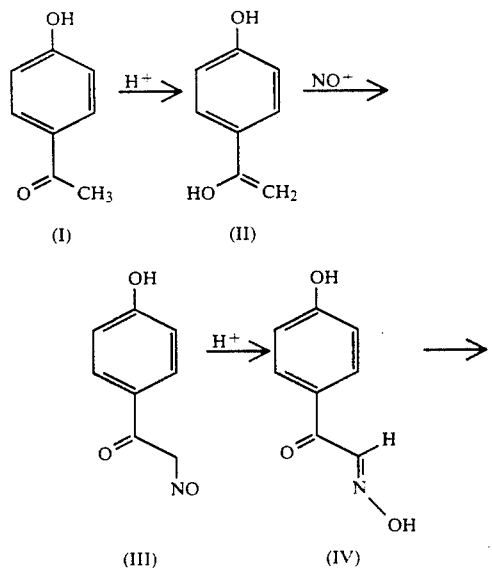

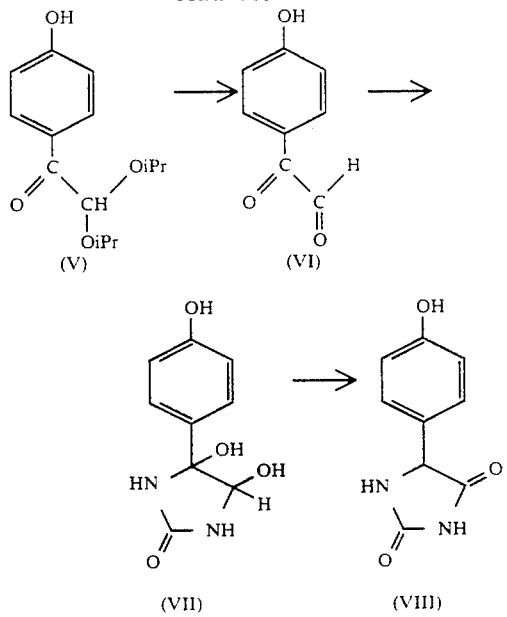

The method of the invention also provides for formation of an hydroxyphenylglycine, wherein the 5-(hydroxyphenyl)hydantoin described above is hydrolyzed to produce the hydroxyphenylglycine.

The invention further provides a method for producing D-hydroxyphenylglycine which comprises optically resolving the hydroxyphenylglycine described above to produce D-hydroxyphenylglycine.

The invention further provides an alternative method for producing D-hydroxyphenylglycine, comprising: enzymatically hydrolyzing the 5-(hydroxyphenyl)-hydantoin previously described to form D-5-(hydroxyphenyl)hydantoic acid, and then decarbamoylating the D-5-(hydroxyphenyl)-hydantoic acid to form D-hydroxyphenylglycine.

DETAILED DESCRIPTION OF THE PREFERRED EMBODIMENT

In the practice of the present invention, one begins the procedure of producing 5-(4'-hydroxyphenyl)-hydantoin by reacting a mixture which is broadly composed of 4-hydroxyacetophenone, a $C_1$ to $C_{10}$ alkyl nitrite, a primary or secondary alcohol, and a strong mineral acid such as hydrogen chloride to form an intermediate, hydroxyaromatic ketoacetal. Preferably the reaction mixture is substantially free from the presence of water.

The $C_1$ to $C_{10}$ alkyl nitrite, which is typically methyl nitrite, isopropyl nitrite or t-butyl nitrite. This reaction mixture component is preferably present in an amount of from about 1 to about 3 mole equivalents of the amount of 4-hydroxyacetophenone, more preferably from about 1 to about 2.5 mole equivalents and most preferably from about 1 to about 2.0 mole equivalents.

The primary or secondary alcohol is typically methyl alcohol, isopropyl alcohol, sec-butyl alcohol, or n-butyl alcohol. It is preferably present in a large excess of that amount required for the reaction or from about 2 to about 10 times the weight of the 4-hydroxyacetophenone or more preferably from about 2 to about 5 times the weight of the 4-hydroxyacetophenone.

The strong mineral acid is preferably hydrogen chloride or sulfuric acid. Theoretically, the acid should be present in at least a catalytic amount, however, it is preferably present in the composition in an amount of from about 0.1 to about 6 mole equivalents of the amount of 4-hydroxyacetophenone, more preferably from about 0.1 to about 3 mole equivalents and most preferable from about 0.1 to about 2 mole equivalents.

It presently appears that the components of the reaction mixture used to form the hydroxyaromatic ketoacetal may be combined in any order. The reaction is exothermic and requires no heating to drive the reaction. The reaction may be cooled to a convenient working temperature. In the preferred embodiment, the reaction is conducted at a temperature of from about −20° C. to about 50° C., or more preferably from about −10° C. to about 40 or most preferably from about −10° C. to about 25° C.

In the preferred embodiment, the reaction to form the hydroxyaromatic ketoacetal is conducted for a time period ranging from about 1 hour to about 24 hours, or more preferably from about 1 hour to about 8 hours, and most preferably from about 1 hour to about 4 hours.

The hydroxyaromatic ketoacetal, for example the dialkylacetal of 4-hydroxyphenylketoaldehyde (the dialkylacetal of 4-hydroxyphenylglyoxaldehyde), is then hydrolyzed to produce hydroxyphenylketoaldehyde (hydroxyphenylglyoxal). The acetal of interest is added to water that has been previously acidified with any nonoxidizing acid, such as HCl or $H_2SO_4$, to a pH around O. (An organic cosolvent can also be used in combination with the water, cosolvents such as dioxane and acetonitrile are known to work.) The acetal can be solid or in solution. Under atmospheric pressure, wate and alcohol are removed by distillation during the reaction, to drive the reaction, until the conversion to hydroxyphenylglyoxal is complete. Generally, the alcohol (preferably methanol, isopropanol and n-butanol) will be lower boiling than water, but any alcohol that azeotropes works as well. As an alternative, acetic acid can be used as the reaction solvent rather than water so long as sufficient water is present for hydrolysis. When acetic acid is used, this acid is distilled off prior to any subsequent reaction of the hydroxyphenylglyoxal of the kind described below.

In the preferred embodiment for production of hydroxyphenylketoaldehyde from hydroxyaromatic ketoacetal, the water is present in the mixture in a large excess of that amount required for the reaction, preferably from about 0.1 to about 3 times the weight of the hydroxyaromatic ketoacetal, or more preferably from about 0.5 to about 2.5 times the weight of the alcohol, and most preferably about 0.5 to about 1 5 times the weight of the alcohol.

In the preferred embodiment for forming the hydroxyaromaticketoaldehyde, the concentrated mineral acid is theoretically present in at least a catalytic amount, however, it is preferably present in the composition in an amount of from about 0.1 to about 8 mole equivalents of the amount of 4-hydroxyacetophenone used initially or the 4-hydroxyphenylketoacetal, more preferably from about 0.1 to about 4 mole equivalents and most preferably from about 0.1 to about 2 mole equivalents.

The hydroxyaromatic ketoaldehyde (hydroxyphenylglyoxal) can then be reacted with water, urea and concentrated mineral acid to produce 5-(hydroxyphenyl)hydantoin. In the preferred embodiment, the urea is present in an amount of from about 1 to about 4 mole equivalents of the amount of 4-hydroxyacetophenone used initially or the 4-hydroxyphenylglyoxaldehyde, more preferably from about 1 to about 3 mole equivalents and most preferably from about 1 to about 2 mole equivalents.

Further it appears that the components of the reaction to convert the hydroxyphenylketoacetal to 5-(hydroxyphenyl)-hydantoin may be combined in any order. Thus, the hydroxyphenylketoacetal can be reacted with water to prepare hydroxyphenylketoaldehyde and subsequently reacted to produce the hydantoin, or the hydroxyphenylketoacetyl can be combined with all of the reactants necessary to permit direct conversion to the hydantoin. This reaction step does require heating to drive the reactions. In the preferred embodiment, the reaction is conducted at a temperature of from about 40° C. to about 100° C., or more preferably from about 50° C. to about 100° C., and most preferably from about 50° C. to the reflux temperature of the solution.

In the preferred embodiment, the reaction to form 5-(hydroxyphenyl)hydantoin is conducted for from about 0.5 hour to about 24 hours, or more preferably from about 0.5 hour to about 8 hours, and most preferably from about 1 hour to about 5 hours.

In the preparation of hydroxyphenylglycine, such a 5-(4'-hydroxyphenyl)hydantoin prepared as described above is hydrolyzed. Methods of hydrolysis are known in the art per se. The hydrolysis may be conducted by reacting the crude 5-(4'-hydroxyphenyl)hydantoin with an aqueous sodium hydroxide solution containing hydroxylamine yielding 5-(4'-hydroxyphenyl)hydantoic acid. Upon treatment with nitrous acid, p-hydroxyphenylglycine is formed.

Resolution

There are many optical resolution techniques known in the art whereby a racemic mixture of DL-p-hydroxyphenylglycine can be resolved to D-p-hydroxyphenylglycine. Such may be performed with d-3-bromocamphor-3-sulfonic acid; aromatic sulfonic acids, such as benzenesulfonic acid, o-toluenesulfonic acid, p-toluenesulfonic acid, p-ethylbenzenesulfonic acid, sulfosalicylic acid, and 2-naphthol-6-sulfonic acid; and (+)- phenylethanesulfate. In an alternative method, DL-5-(4-hydroxyphenyl)hydantoin can be converted into D-N-carbamoyl-(4-hydroxyphenyl)glycine, i.e. D-(4-hydroxyphenyl)hydantoic acid and the latter is then decarbamoylated into D-4-hydroxyphenylglycine.

It is known from U.S. Pat. No. 3,094,741, that DL-5-(4-hydroxyphenyl)hydantoin can be converted into D-N-carbamoyl-(4-hydroxyphenyl)glycine by causing cells or treated cells of specific microorganisms to act on the hydantoin in an aqueous medium at pH 7 to 10. D-N-carbamoyl-(4-hydroxyphenyl)glycine can be converted into D-4-hydroxyphenylglycine by decarbamoylation by reacting D-N-carbamoyl-(4-hydroxyphenyl)glycine with an equimolar amount of nitrous acid in the presence of a strong acid.

A racemic mixture of p-hydroxyphenylhydantoin may be converted to D-p-hydroxyphenylglycine according to the method of Takahashi, *Microbial Production of D-p-Hydroxyphenylglycine*, Prog. Ind. Microbial., 24 (Biotechnol. Amino Acid Prod.), 269-279 (1986), which in incorporated herein by reference.

Transformation of p-hydroxyphenylhydantoin into
N-Carbamoyl-D-hydroxyphenylglycine
(D-hydroxyphenylhydantoic acid)

Enzyme Preparation

For the industrial production of D-p-hydroxyphenylglycine, the microorganism employed in the asymmetric hydrolysis of p-hydroxyphenylhydantoin is selected from wild strains by examining the hydantoinase activity and its stereoselectivity. Such microorganisms can be found in a side range of genera, high activity is especially found in bacteria. Cells with high hydantoinase activity can be obtained by culturing the microorganism in a medium supplemented by pyrimidine base or their metabolites such as uracil, thymine, or Beta-Alanine as the inducer. The accumulation of hydantoinase in cells is further increased, when a metal ion such as manganese, nickel, or magnesium is added in the medium together with the inducer.

Asymmetric Hydrolysis of p-Hydroxyphenyl Hydantoin

In the reaction of the asymmetric hydrolysis of p-hydroxypheynlhydantoin, racemic p-hydroxyphenyl hydantoin can be completely transformed into N-carbamoyl-D-p-hydroxyphenylglycine by the action of microbial hydantoinase. Generally hydantoins are readily racemized in dilute alkaline solution through the mechanism of base catalysis. In practice, p-hydroxyphenyl hydantoin undergoes spontaneous racemization very easily under mild conditions such as those of the enzymatic reaction. In the reaction system of the asymmetric hydrolysis of p-hydroxyphenylhydantoin, only D-form p-hydroxyphenylhydantoin is susceptible to the enzymatic hydrolysis. Unreactive L-p-hydroxyphenylhydantoin undergoes rapid spontaneous racemization in the same system. However, the N-carbamoyl-D-p-hydroxyphenylglycine formed is never racemized under these conditions. Consequently, in this system, the enzymatic hydrolysis of the hydantoin ring and chemical racemization of the substrate proceed simultaneously, so that DL-p-hydroxyphenyl hydantoin can be completely transformed into D-form N-carbamoyl-p-hydroxyphenylglycine.

The microorganism is employed in a form of cultured broth, with intact cells or treated cells used as an enzyme for the hydrolysis. In may cases, the smooth reaction can be performed by using the cultured broth as is. The high concentration of the substrate DL-p-hydroxyphenylhydantoin is available to the reaction depending upon the activity of microorganism used. A large portion of p-hydroxyphenylhydantoin is present in suspended form, since the solubility of p-hydroxyphenylhydantoin in water is very low (50–75 mM) However, the substrate is successively dissolved in the progress of the reaction in alkaline pH. It is preferable to maintain the pH by adding alkaline solution successively, since the pH is lowered in the course of hydrolysis and the drop in pH will result in lowering the reaction rate. It is also effective to cover the reaction mixture with an inert gas such as nitrogen to avoid oxidative side reaction of phenol nucleus Under these optimum conditions, the yield of N-carbamoyl-D-p-hydroxyphenylglycine formed is almost quantitative.

Decarbamoylation of
N-Carbamoyl-D-p-Hydroxyphenylglycine

N-Carbamoyl-D-p-hydroxyphenylglycine produced by the enzymatic hydrolysis can be readily converted into D-p-hydroxyphenylglycine by decarbamoylation with nitrous acid under acidic conditions. The principle of this oxidative reaction is based on the Van Slyke determination, and the reaction seems to be a consecutive reaction as follows. With respect to the stereochemistry of the reaction, the retention of the configuration is achieved completely. Therefore, optically pure D-p-hydroxyphenylglycine can be readily obtained in good yield. The decarbamoylation is preferably carried out by reacting N-carbamoyl-D-p-hydroxyphenylglycine with an approximately equimolar nitrous acid in an aqueous medium in the presence of a strong mineral acid such as sulfuric or hydrochloric acid. It is convenient to employ a water-soluble salt of nitrous acid such as sodium nitrite or potassium nitrite. Since this decarbamoylation is an exothermic reaction and generates large quantities of gas ($N_2$ and $CO_2$), an aqueous solution of nitrous acid is added gradually to the rection medium with agitation to perform the smooth reaction. The reaction temperature is usually kept below 20.C in order to avoid a side reaction such as the further degradation of D-p-hydroxyphenylglycine into 4-hydroxymandelic acid and others. Under these optimum conditions, the yield of D-p-hydroxyphenylglycine is almost guantitative. A chemicoenzymatic process, attractive from economical and technical standpoints, was developed for the production of D-p-hydroxyphenylglycine. In the first step of the process, DL-p-hydroxyphenylhydantoin is synthesized. In the second step, DL-p-hydroxyphenyl hydantoin is completely hydrolyzed into N-carbamoyl-D-p-hydroxyphenylglycine by microbial hydantoinase. In the third step, N-carbamoyl-D-p-hydroxyphenylglycine is then transformed into D-p-hydroxyphenylglycine by chemical reaction. This simplified process provides high optically pure D-p-hydroxyphenylglycine in high yield.

The following non-limiting examples serve to illustrate the invention.

EXAMPLES

Preparation of 5-(4'-Hydroxyphenyl)hydantoin from 4-Hydroxyacetophenone in a Single Pot Reaction.

Example 1

A 250 ml three neck round bottom flask was charged with 100 ml isopropanol and sparged with HCl for 5 minutes. Then 20 g of 4-hydroxyacetophenone were added forming a red solution. The flask was then fitted with a thermowell, a reflux condenser and an addition funnel containing 22 ml of crude isopropyl nitrite and 20 ml isopropanol. The reflux condenser was fitted with an oil filled U-tube and the contents were heated with a water bath to 40° C. The contents of the addition funnel were added dropwise over a one hour period while the temperature was held between 40°–50° C. The contents are held at 50° C. for 4 hours and then allowed to stand at room temperature overnight. The next morning 18 g of urea were slurried with 20 ml water and then added to the flask followed by 18 ml of concentrated HCl. The contents were refluxed for 5 hours and then allowed to stand overnight. The next day the solids were filtered, washed with 100 ml water and then dried in a vacuum oven at 60° C. overnight yielding 18 g of light yellow solids. HPLC analysis revealed that the solids were about 56% 5-(4'-hydroxyphenyl)hydantoin.

Example 2

A 2000 ml three neck round bottom flask was charged with 500 ml isopropanol and gently sparged with HCl for 5 minutes. Then 100 g of 4-hydroxyacetophenone were added and dissolved with stirring. The flask was then fitted with a thermowell, a reflux condenser and an addition funnel containing 110 ml of crude isopropyl nitrite and 110 ml isopropanol. An ice bath was placed around the flask and the contents of the addition funnel were added dropwise while stirring over a 1 hour period. The temperature was held between 4°–8° during the addition. After the addition was complete the contents were sparged with HCl for 5 minutes and then allowed to stand stirring at room temperature for 1.5 hours. Then a slurry of 90 g urea and 100 ml water were added to the flask followed by 90 ml concentrated HCl. The contents were then refluxed for 1.5 hours and allowed to stand overnight at room temperature. The next day the slurry was cooled to 5° C. and filtered. The solids were then dried on a rotovap at 60° C. for 1 hour yielding 86 g of solids which proved to be about 72% 5-(4'-hydroxyphenyl)hydantoin by HPLC.

Example 3

A 500 ml three neck round bottom flask was fitted with a thermowell, a reflux condenser (capped with an oil filled U-tube), and an addition funnel. The flask was charged with 100 ml of 13.5% by weight HCl/isopropanol solution and 40 g 4-hydroxyacetophenone. The addition funnel was charged with 36 ml of crude isopropyl nitrite and 36 ml isopropanol. An ice bath was placed around the stirred flask and the contents of the addition funnel were added dropwise over a 2 hour period while holding the temperature between 0°–10° C. After the addition was complete the contents were allowed to stir at room temperature for 2 hours. Then 40 g of urea were dissolved in 40 ml water and added to the flask, followed by 20 ml of concentrated HCl. The contents were then refluxed for 1 hour and allowed to stand stirring at room temperature overnight. The next day the slurry was cooled to 5° C., filtered and washed with 100 ml cold water. The solids were dried on the rotovap at 60° C. for 2 hours yielding 25.5 g of material which proved to be about 70% 5-(4'-hydroxyphenyl)-hydantoin by HPLC.

Example 4

A 500 ml three neck round bottom flask was fitted with a thermowell, a reflux condenser (capped with an oil filled U-tube), and an addition funnel. The flask was charged with 25 ml of 28.3% HCl/isopropanol solution, 50 ml isopropanol, and 40 g 4-hydroxyacetophenone. The addition funnel was charged with 36 ml of crude isopropyl nitrite and 36 ml isopropanol. The flask contents were stirred and cooled with an ice bath while the contents of the addition funnel were added dropwise over a 2 hour period. During the addition the temperature was held between 5°–10° C.

The contents were then allowed to stand stirring at room temperature for 2 hours. Next 40 g of urea were dissolved in 80 ml of water and added to the flask followed by 25 ml concentrated HCl. The contents were refluxed for 2 hours and during this time 125 ml of distillate removed. The slurry was cooled to 5° C. and the solids were filtered and washed with 100 ml cold water. After drying in the rotovap at 60° C. for 2 hours, 38.7 g of material were recovered. HPLC analysis revealed that the material was 68.8% 5-(4'-hydroxyphenyl)hydantoin.

Example 5

A 250 ml round bottom flask was fitted with a thermowell, a reflux condenser (capped with an oil filled U-tube), and an addition funnel. The flask was charged with 25 ml of 28.3% HCl/isopropanol solution, 57 ml isopropanol, and 20 g 4-hydroxyacetophenone. The addition funnel was charged with 20 ml t-butyl nitrite. A water bath was placed around the flask and the contents stirred while the t-butyl nitrite was added in 2-3 ml portions over a 30 minute period and the temperature was held between 20°–40° C. The contents were allowed to stir at room temperature for 30 minutes and an additional 4 ml of crude t-butyl nitrite were added followed by 25 ml of 28.3% HCl/isopropanol solution. The contents of the flask were allowed to stand stirring at room temperature over the weekend. Then 20 g of urea were added and allowed to stir for 10 minutes.

Next, 50 ml of water and 15 ml concentrated HCl were added and the contents refluxed for 4 hours. After refluxing, the slurry was cooled to 5° C. and the solids were filtered and washed with 25 ml cold water. The solids were dried overnight in the vacuum oven at 60° C. yielding 15.3 g of material that proved to be about 74% 5-(4'-hydroxyphenyl)-hydantoin.

Example 6

A 250 ml round bottom flask was fitted with a thermowell, a reflux condenser (capped with an oil filled U-tube), and an addition funnel containing 18 ml of crude isopropyl nitrite. The flask was charged with 25 ml of 28.3% by weight HCl/isopropanol solution, 57 ml isopropanol, and 20 g 4-hydroxyacetophenone. The contents of the flask were stirred and a water bath was placed around the flask. Then the contents of the addition funnel were added into the flask in 2-3 ml portions over a 30 minute period while the temperature was held between 20°–30° C. The contents were allowed to stand stirring at room temperature for 30 minutes and an additional 3 ml portions of isopropyl nitrite were added. The contents were then allowed to stir overnight at room temperature and the next day 20 g of urea were added. After stirring for 10 minutes, 50 ml of water and 15 ml concentrated HCl were added. The contents were then refluxed for 4 hours. The resulting slurry was cooled to 5° C. with an ice bath and the solids were filtered and washed with 25 ml cold water. The wet cake was then recrystallized from acetic acid yielding 9.3 g of substantially pure 5-(4'-hydroxyphenyl)hydantoin by HPLC analysis.

Example 7

A 500 ml three neck round bottom flask was fitted with a thermowell, an addition funnel, and a reflux condenser (capped with an oil filled U-tube) The flask was charged with 50 ml of isopropanol, 50 ml of 25% HCl/isopropanol solution, and 40 g 4-hydroxyacetophenone. The contents were cooled in an ice bath and 62 ml of crude isopropyl nitrite placed in the addition funnel. The contents of the addition funnel were added dropwise to the flask over a 60 minute period while stirring and holding the temperature between 0°–10° C. The contents were then allowed to stand stirring at room temperature overnight. The next day 40 g of urea were dissolved in 100 ml of water and added to the flask. After stirring for 15 minutes, 20 ml of concentrated HCl were added to the flask and the contents refluxed for 4 hours. During this time 100 ml of distillate was removed from the flask. After the reflux is completed, the contents were cooled to 5° C. and the slurry filtered. The solids were washed with 25 ml of cold water and dried overnight in a vacuum oven at 60° C. yielding 38 g of solids which proved to be 72.3% 5-(4'-hydroxyphenyl)-hydantoin by HPLC analysis.

Example 8

A 250 ml round bottom flask was fitted with a thermowell, an addition funnel, and a reflux condenser (capped with an oil filled U-tube). The flask was charged with 57 ml isopropanol, 25 ml of 28.3% HCl/isopropanol solution and 20 g 4-hydroxyacetophenone. The addition funnel was charged with 20 ml of t-butyl nitrite and the contents of the flask were stirred. The contents of the additional funnel were added to the stirred flask in 2–3 ml portions over a 30 minute period while the temperature was held between 20°–40° C. After the addition was complete, the contents were allowed to stand stirring at room temperature for 30 minutes, then an additional 4 ml of t-butyl nitrite were added followed by 25 ml of 28.3% HCl/isopropanol solution. The contents were allowed to stand stirring over the weekend at room temperature. Then 20 g of urea were added to the flask and the contents were stirred for 10 minutes at which time 50 ml of water, and 15 ml of concentrated HCl were added to the flask. The contents were refluxed for 4 hours and then cooled to 5° C. and the slurry filtered. The solids were washed with 25 ml of cold water and dried in a vacuum oven at 60° C. overnight yielding 15.3 g of material which proved to be 73.5% 5-(4'-hydroxyphenyl)hydantoin by HPLC analysis.

Conversion of 4-hydroxyacetophenone to 4-Hydroxyphenylglyoxal Dimethyl Acetal, Followed by Conversion of the Acetal to 5-(4'-Hydroxyphenyl)hydantoin.

Example 9

A 250 ml three neck Flask A was equipped with a mechanical stirrer, a connector to a peristaltic pump assembly, and an elbow tube for attachment to a second Flask B. Flask A was positioned adjacent to a 1000 ml three neck Flask B which was connected to Flask A using tygon tubing. The 250 ml Flask A was charged with 57 g NaNO₂ and 40 ml MeOH. Flask A was cooled thoroughly using an ice/water bath. Eighty-four (84) ml of 12 M HCl was placed in a reservoir linked to the peristaltic pump for transference to Flask A.

Flask B was fitted with a glass adapted fritt sparger, a stir bar, a dry ice acetone cold finger connected to a bubbler, and a thermowell. Two hundred (200) ml of anhydrous MeOH were charged to this flask and 8.0 g (+/−0.5 g) of HCl vapors were then sparged into the 200 ml of MeOH. Flask B was then cooled using an ice and acetone bath to a temperature ranging between 0 and −2° C.

Fifty (50) g (0.367 mol) of 4-hydroxyacetophenone (4-HAP) was added to Flask B.

The NaNO₂ suspension in Flask A was stirred at a low speed and the 84 g of HCl was added slowly over a 2 hour time period using the peristaltic pump. As the HCl was added to Flask A, a gas comprised of MeONO was formed. This gas passed through the tygon tubing into Flask B. Once the HCl addition to Flask A was complete, the agitation (stirring) rate in Flask B was increased substantially and the agitation was carried out for a time period of one to two minutes, after which Flask A and Flask B were disconnected. Samples from Flask B were analyzed by LC which indicated a yield of 4-hydroxyphenylglyoxal dimethyl acetal of about 88–97% by weight based on the 4-hydroxyacetophenone.

Subsequently, to Flask B was added a mixture of urea (37.4g, 0.62 mol), water (250 ml), and 12 M HCl (10 ml). The contents of Flask B were then stirred at atmospheric pressure under a nitrogen blanket. The temperature was reflux temperature for the contents of Flask B and the reaction time period typically ranged between 18 and 36 hours. The reaction mixture of Flask B was concentrated by removing 160 ml of MeOH by distillation. The mixture residue was chilled overnight at about 0°–5° C. to promote full crystallization of 5-(4'-hydroxyphenyl)hydantoin. The crystallized 5-(4'-hydroxyphenyl)hydantoin was collected by suction filtration, washed with chilled water, and dried in vacuo at 60° C. Analysis by LC showed that a yield of about 80% by weight of 5-(4'-hydroxyphenyl)hydantoin based on the 4-hydroxyacetophenone.

Hydrolysis of Hydroxyaromatic Ketoacetal to Hydroxyaromatic Ketoaldehyde. Conversion of 4-Hydroxyacetophenone to 4Hydroxyphenylglyoxal Example 10

Two hundred and seventy-two (272) grams of 4-hydroxyacetophenone (4-HAP) were charged into a 2 liter, three neck flask containing 600 ml of 1.25 M HCl in methanol. The reactor was fitted with a Friedrich condenser, gas inlet tube below the surface of the methanol, thermowell and magnetic stirrer. Methyl nitrite, generated in a separate reactor by adding diluted sulfuric acid to a methanolic slurry of sodium nitrite, was introduced through the gas inlet. The rate of adding sulfuric acid was used to control the addition of methyl nitrite. The temperature was maintained at <15° C. in the 4-HAP reaction flask.

After the oxidation of 4-HAP to 4-hydroxyphenylglyoxaldimethyl acetal (HPGMA) was complete, the reaction was quenched with an equal volume of water. Most of the methanol was removed under vacuum. The resulting aqueous solution was placed in a round bottom flask set up for distillation. The solution was heated to boiling and the distillation head temperature was monitored. Upon reaching 100° C., the solution was checked by HPLC and found to contain no starting material (HPGMA). Cooling of the residue in the boiling flask to around 4°–5° C. (with stirring) crystallized out the HPGO (416.9 grams; assay-48.3% HPGO, 47.5% H₂O; 1.2 moles 4-hydroxyphenylglyoxal (HPGO), 60% isolated yield). Analysis of the filtrate indicated 56.6 g of HPGO, to give a total of 1.54 moles or 76.8% yield of HPGO, based on 4-HAP.

Example 11

4-HAP (68 grams, 0.5 mole) was charged into a 500 mL three neck flask containing 200 mL of 1 M HCl in methanol. The reactor was fitted with a Friedrich condenser, gas inlet tube below the surface of the methanol, thermowell and magnetic stirrer. Nitrosyl chloride, generated in a separate reactor by adding 40% aqueous NaNO$_2$ (259 grams, 1.5 mole) to concentrated HCl (360 mL, 3 moles), was introduced through the gas inlet. The rate of adding sodium nitrite was used to control the addition of nitrosyl chloride. The temperature was maintained at <5° C. in the 4-HAP reaction flask.

After the oxidation of 4-HAP to HPGMA was complete, the reaction was quenched with an equal volume of water. Most of the methanol was removed under vacuum. The resulting aqueous solution was placed in the refrigerator (−5° C.). After cooling overnight, a yellow solid was filtered off. Drying in the vacuum oven yielded HPGO (87.6% pure, 28.9 grams, 0.15 mole, 30% yield). The filtrate was assayed to contain 11.5% HPGO (350 grams, 40.25 grams HPGO, 0.24 mole). Final yield of HPGO was 0.39 mole, 78%.

Preparation of p-Hydroxyphenylglycine from 5-(4'-Hydroxyphenyl)hydantoin.

Example 12

A 250 ml round bottom flask is charged with 10 g of crude 5-(4'-hydroxyphenyl)hydantoin (ca. 74.5% pure), 8 g NaOH, 5 g hydroxylamine sulfate, and 100 ml of water. The contents are stirred to dissolve the solids and then brought to reflux. After refluxing for 30 minutes, the solution is hot filtered through a pad of Celite. Then 60 ml of concentrated HCl are added to the filtrate and the solution cooled in an ice bath. The cold slurry is filtered and the solids washed with 50 ml of cold water. The solids are dried in a vacuum oven at 60° C. overnight yielding 6.0 g of essentially pure 5-(4'-hydroxyphenyl)hydantoic acid. A 2 g sample of the 5-(4'-hydroxyphenyl)hydantoic acid is dissolved in 20 ml of concentrated hydrochloric and cooled in an ice bath. Over a 45 minute period 6.5 g of 10% aqueous sodium nitrite solution is added dropwise to the flask (while still in the ice bath). The contents are allowed to stand for 1 hour in the ice bath and then concentrated on the rotovap at 75° C. The pH is then adjusted to 4 with concentrated ammonium hydroxide. The slurry is cooled in an ice bath and then filtered. The solids are washed with 30 ml of cold water and dried in an oven at 145° C. for 1 hour yielding 1.3 g of material which proves (via HPLC) to be ca. 65.1% p-hydroxyphenylglycine and ca. 27.9% unreacted 5-(4'-hydroxyphenyl)hydantoic acid.

Preparation of p-Hydroxyphenylhydantoic Acid

Example 13

Crude 5-(p-hydroxyphenyl)hydantoin (85.6 g) is placed in a 1-liter round bottom flask with 41 g hydroxylamine sulfate, 1 g Na$_2$S$_2$O$_4$, 60 g NaOH, and 300 ml H$_2$O. The contents are refluxed for 1 hour and then cooled in an ice bath. Then 125 ml cold concentrated HCl are added. The solids are filtered and washed with 200 ml H$_2$O. The solids are dried in a vacuum oven at 60° C. over the weekend yielding 58.8 g of ca. 95% pure p-hydroxyphenylhydantoic acid (by HPLC analysis).

Hydrolysis of p-Hydroxyphenylhydantoic Acid

Example 14 p-Hydroxyphenylhydantoic acid (19 g) is dissolved in 200 ml of cold concentrated HCl in a 500 ml flask. The flask is cooled in an ice bath and a solution of 6.5 g NaNO$_2$ in 56 ml H$_2$O is added dropwise over a 45 minute period while the temperature is held between 0°–8° C. The solution is allowed to stand stirring in the ice bath for 2½ hours and then stand at room temperature overnight. The next day the pH is adjusted to −5 with concentrated NH$_4$OH. The solution is concentrated on a rotovap to −250 ml. The slurry is cooled in an ice bath and then filtered. The solids are washed with 2×25 ml portions of ice water. The solids are then placed in a round bottom flask with 700 ml water and 1 g activated carbon. The contents are stirred and refluxed for 30 minutes, and then hot filtered through a pad of Celite. The solution is concentrated on a rotovap to −350 ml (the cloud point) and then cooled in an ice bath. The white solids are filtered and washed with 50 ml ice water. After drying in a vacuum oven (60° C.) over the weekend 6.2 of white needles with a mp 222° C. is obtained. HPLC analysis reveals the sample is 99.8% pure p-hydroxyphenylglycine.

REFERENCE EXAMPLE 1

D-Hydroxyphenylglycine may be resolved according to the method described in Yamada, et al, "Preparation of D-p-Hydroxyphenylglycine. Optical Resolution of DL-p-Hydroxyphenylglycine with d-3-Bromocamphor-8-Sulfonic Acid", Agric. Biol. Chem. 43(2), 395–396, 1979, which is incorporated herein by reference D-camphor ([a]$_D^{20}$−44.0°, c=7.5), in ethanol is prepared as follows Bromine (320 g) is added dropwise to d-camphor (304 g) at 80° C. over a period of three hours under stirring and the liquified reaction mixture is kept at the same condition for 3 hours. After hydrogen bromide is released by bubbling, the reaction mixture is poured into ice water (3 liters) and the resulting precipitate is recrystallized from ethanol (230 mol) to give d-3-bromocamphor (302 g), mp 76° C. [a]$_D^{20}$−134° (c=10, EtOH). d-3-bromocamphor (231 g) is dissolved in chloroform (400 ml) and chlorosulfonic acid (233 g) are added dropwise to this solution over 1 hour at 50° C. The reaction mixture is refluxed for 12 hours and poured into iced water (1 liter). The layer and washings are neutralized with Ca(OH)$_2$ (120 g), and precipitated CaSO$_4$ is filtered off. To the filtrate (NH$_4$)$_2$CO$_3$ (128 g) are added and the precipitated CaCO$_2$ is removed. The filtrate is concentrated and crystallized crude ammonium d-bromocamphor sulfonic acid (152 g) is recrystallized from water (270 ml) to give ammonium d-bromocamphor sulfonic acid (102 g), mp. 270°–272° C.(dec), [a]$_D^{20}$−85.3° (c=2, water), lit.[a]$_D^{22}$−85.3° (c=4, water), [a]$_D^{20}$−84.5° (c=1.6, water). Calculated for NH$_4$C$_{10}$H$_{14}$O$_2$4SBr: C, 36.59: H, 5.53: N, 4.27. Ammonium d-bromocamphor sulfonic acid obtained above is passed through Amberlite IR-120, and the effluent is concentrated to dryness and used as free d-bromocamphor sulfonic acid monohydrate. Analysis: All samples are dried overnight in vacuo at 40° C. Melting points are measured with a Yamato MP-21 melting point apparatus in an unsealed capillary tube and are uncorrected. Optical rotations are measured with a Perkin-Elmer 141 automatic polarimeter.

Optical Resolution DL-p-hydroxyphenylglycine with d-3-bromocamphor-3-sulfonic acid A mixture of DL-hydroxyphenylglycine (30.0 g) and d-bromocamphor sulfonic acid monohydrate (59.1 g) is dissolved in water (290 ml) at 95° C. and stirred at 25° C. for 2 hours. The precipitated crystals are filtered, washed with a small amount of cold water and dried to give crude D-p-hydroxyphenylglycine·d-bromocamphor sulfonic acid (40.2 g), [a]$_D^{23}$−4.9° (c=1, 1N HCl).

The crude salt (40.0 g) is recrystallized from 0.5° d-bromocamphor sulfonic acid aqueous solution (300 ml) to give D-p-hydroxyphenylglycine·d-bromocamphor sulfonic acid (35.5 g), $[a]_D^{23} -2.9°$, (c=1, 1N HCl), mp 243°-245° C. (dec). Analysis - Found: C, 45.17; H, 5.11; N, 2.93; S, 6.94. The product is optically and chemically pure. The specific rotation of a mixture of DL-p-hydroxyphenylglycine and equivalent amount of d-bromocamphor sulfonic acid is $[a]_D^{23} -54.7°$ (c=1, 1N HCl) and that of authentic DL-p-hydroxyphenylglycine is $[a]_D^{23} -2.9°$ (c=1, 1N HCl).

Preparation of D-p-Hydroxyphenylglycine

The pure D-p-hydroxyphenylglycine·d-bromocamphor sulfonic acid (30.0 g) obtained above is dissolved in water (250 ml) at 95° C. The solution is adjusted at pH 6 with 2N NaOH (ca. 31 ml), concentrated to about 70 g and stirred at 5° C. for 2 hours. The precipitated crystals are filtered, washed with water and dried to give D-p-hydroxyphenylglycine (9.6 g), $[a]_D^{25} -158.3°$ (c=1, 1N HCl). Analysis - Found C, 57.70; H, 5.41, N, 8.33 calculated for $C_6H_9NO$, C, 57.48; H, 5.43, N, 8.38°.

Recovery of Optically Pure
L-p-Hydroxyphenylglycine

After the separation of less soluble D-p-hydroxyphenylglycine·d-bromocamphor sulfonic acid in the above resolution process, the mother liquor is adjusted at pH 6 with 2N NaOH, concentrated to about 130 g and stirred at 5° C. for 2 hours. The precipitated crystals are filtered, washed with water, and dried to give dried to give optically impure L-p-hydroxyphenylglycine (12.6 g) $[a]_D^{25} -129.3°$ (c=1, 1N HCl).

Racemization of optically impure
L-p-Hydroxyphenylglycine

Optically impure L-p-hydroxyphenylglycine (10.0 g) obtained by the above procedure is dissolved in 2N HCl (30 ml). The mixture is heated in an autoclave at 140° C. for 12 hours. After the reaction, the mixture is adjusted at pH 6 with 2N NaOH and is stirred at 5° C. for 2 hours. The precipitated crystals are filtered, washed with water and dried to give DL-p-hydroxyphenylglycine (9.2 g), $[a]_D^{25} -0.0°$ (c=1, 1N HCl). The racemized p-hydroxyphenylglycine can be reused for resolution.

Reuse of d-3-bromocamphor-8-sulfonic acid

The sodium salt of d-bromocamphor sulfonic acid contained in the mother liquor after the separation of D- and L-p-hydroxyphenylglycine can be reused as a resolving agent by addition of an equivalent amount of hydrochloric acid. In the mother liquor, after the separation of D-p-hydroxyphenylglycine (9.6 g) in the preceding procedure, DL-p-hydroxyphenylglycine (9.1 g) and 2N HCl (31 ml) are added. The mixture is heated at 95° C. for dissolution and stirred at 25° C. for 2 hours. The precipitated crystals are filtered, washed with a small amount of cold water, and dried a give crude D-p-hydroxyphenylglycine·d-bromocamphor sulfonic acid (14.7 g) $[a]_D^{25} -3.9°$ (c=1, 1N HCl).

REFERENCE EXAMPLE 2

Optical Resolution of DL-p-hydroxyphenylglycine

The following resolution method is suggested by Yamada, et al, "Preparation of D-p-hydroxyphenylglycine: Optical Resolution of DL-p-hydroxyphenylglycine By Preferential Crystallization Procedure", Agric. Biol. Chem., 42(8), 1521-6, 1978, which is incorporated herein by reference.

In this example, D-, L-, and DL-p-hydroxyphenylglycine manufactured by Tanabe Seiyaku Co. Ltd. are used. Aromatic sulfonic acids, i.e. benzenesulfonic acid. o-toluenesulfonic acid, p-toluenesulfonic acid, p-ethylbenzenesulfonic acid, sulfosalicylic acid, and 2-naphthol-6-sulfonic acid are obtained from Tokyo Kasei Kogyo Co., Ltd. All samples are dried overnight in vacuo at 40° C. Melting points are measured with a Yamato MP-21 melting point apparatus in an unsealed capillary tube and are uncorrected. Infrared spectra of samples are determined in KBr with a Shimazu infrared spectrophotometer, Model IR-27G. Optical rotations are measured with a Perkin-Elmer 141 automatic polarimeter. Elemental analyses are performed by using a Perkin-Elmer 240 elemental analyzer. Solubility is determined by approaching saturation equilibrium from the both sides of undersaturation and supersaturation. Solute concentration is measured with a Karl Zeiss immersion refractometer.

Preparation of aromatic sulfonates of
p-hydroxyphenylglycine

Aromatic sulfonates of p-hydroxyphenylglycine are prepared from p-hydroxyphenylglycine and an equimolar amount or a slight excess of the corresponding aromatic sulfonic acids in aqueous solution. In the case of DL-p-hydroxyphenylglycine o-toluenesulfonic acid, a mixture of DL-p-hydroxyphenylglycine (200.0 g) and 1.05 equimolar amount of o-toluenesulfonic acid.$2H_2O$ (261.6 g) are dissolved in water (800 ml) by heating, treated with charcoal and cooled in a refrigerator. The resulting precipitates and the second crop obtained by concentration of the mother liquor to about a half volume are collected, washed with cold water and dried. The total yield of DL-p-hydroxyphenylglycine·o-toluenesulfonic acid is 393.5 g (96.9%). The products are almost pure and can be used for optical resolution without further purification. D-and L-p-hydroxyphenylglycine-o-toluenesulfonic acid are prepared in the same way. The racemic modifications and the optically active isomers of p-hydroxyphenylglycine·benzenesulfonic acid, p-hydroxyphenylglycine·p-toluenesulfonic acid, p-hydroxyphenylglycine·p-ethylbenzenesulfonic acid, p-hydroxyphenylglycine·sulfosalicylic acid·$H_2O$, and p-hydroxyphenylglycine·2-naphthol-6-sulfonic acid are similarly prepared as above in a high yield (85-95%). For elemental analysis and determination of properties, p-hydroxyphenylglycine·o-toluenesulfonic acid, p-hydroxyphenylglycine sulfosalicylic acid·$H_2O$, and p-hydroxyphenylglycine·2-naphthol-6sulfonic acid are recrystallized from water. p-hydroxyphenylglycine·benzenesulfonic acid, p-hydroxyphenylglycine·p-toluenesulfonic acid, and p-hydroxyphenylglycine·p-ethylbenzenesulfonic acid are recrystallized from aqueous solutions of 0 5 M benzenesulfonic acid, 0 5 M p-toluenesulfonic acid, and 3 M p-ethylbenzenesulfonic acid, respectively.

Optical resolution

Optical resolution of the aromatic sulfonates of DL-p-hydroxyphenylglycine by the preferential crystallization procedure is carried out in the usual manner. In the case of DL-p-hydroxyphenylglycine·o-toluenesulfonic acid, DL-p-hydroxyphenylglycine·o-toluenesulfonic acid (24.00 g) and D-p-hydroxyphenylglycine·o-toluenesulfonic acid (2.50 g) are dissolved in water (100 ml) at an elevated temperature. The solution is cooled to 30° C., seeded with D-p-hydroxyphenylglycine-o-toluenesulfonic acid (0.10 g), and stirred at the same temperature. By refractometric and polarimetric measurements of the liquid phase, it is observed that preferential crystallization of D-p-hydroxyphenylglycine-o-toluenesulfonic acid remain in the solution. After 70 min, the precipitated crystals are collected by filtration, washed with a small amount of cold water, and dried to give D-p-hydroxyphenylglycine-o-toluenesulfonic acid (5.30 g), $[a]_D^{25}$-64.6° (c=1, water), optical purity 97.0%. In order to adjust the concentration of DL-p-hydroxyphenylglycine-o-toluenesulfonic acid in the mother liquor to the same as that in the previous operation, DL-p-hydroxyphenylglycine o-toluenesulfonic acid (5.38 g) and a small amount of water are added to the mother liquor after the separation of D-p-hydroxyphenylglycine-o-toluenesulfonic acid. Amounts of the added DL-phydroxyphenylglycine are calculated from the analyses of the solution. Thus, the composition of the solution is the same as that in the initial state except that the solution contained the L-isomer in excess. By seeding this supersaturated solution with L-p-hydroxyphenylglycine-o-toluenesulfonic acid (0.10 g), preferential crystallization of L-p-hydroxyphenylglycine-o-toluenesulfonic acid is carried out in the same manner as described above. By repeating these procedures, D- and L-isomers are successively obtained. Other sulfonates of DL-p-hydroxyphenylglycine can also be resolved in the same manner as described above.

Purification of optically impure
D-p-hydroxyphenylglycine-o-toluenesulfonic acid The optical isomers obtained by the above procedure are practically pure. However, if further optical purification is required, it can be performed as follows. Optically crude D-p-hydroxyphenylglycine-o-toluenesulfonic acid (20.00 g, optical purity 82.3%) is mixed with water (28.8 ml) for 20 hours at 20° C. The residual crystals are collected by filtration, washed with a small amount of cold water, and dried to give optically pure D-p-hydroxyphenylglycine -o-toluenesulfonic acid (16.20 g), the yield being 98.4% based on D-isomer in the original optically crude D-p-hydroxyphenylglycine-o-toluenesulfonic acid.

Preparation of optically active
D-p-hydroxyphenylglycine

From the optically pure sulfonates of p-hydroxyphenylglycine obtained above, optically pure p-hydroxyphenylglycine is obtained by neutralization with alkali or by use of ion exchange resins. In the case of p-hydroxyphenylglycine-o-toluenesulfonic acid, optically pure D-p-hydroxyphenylglycine-o-toluenesulfonic acid (14.00 g) is dissolved in water (40 ml) at an elevated temperature and treated with charcoal. The solution is adjusted to pH 6 with 5 N sodium hydroxide and allowed to stand in a refrigerator overnight. The resulting precipitate is collected, washed with water, and dried to give D-p-hydroxyphenylglycine (5.82 g), $[a]_D^{25} - 158.4°$ (c=1, N-HCl). Anal. Calculated for $C_8H_9NO_3$: C, 57.48; H,5.43;N,8.38. Found: C,57.63; H,5.63; N, 8.29.

Preparation of
DL-p-hydroxyphenylglycine-o-toluenesulfonic acid by using recovered o-toluenesulfonic acid To the mother liquor obtained after the separation of D-p-hydroxyphenylglycine in the above experiment, DL-p-hydroxyphenylglycine (5.82 g) is added with 12 N HCl (3.5 ml) and dissolved by heating. The solution is concentrated to about 40 g, and cooled in a refrigerator. The resulting precipitates and the second crop obtained by concentration to about 13 g are collected, washed with cold water, and dried. The total yield of DL-p-hydroxyphenylglycine-o-toluenesulfonic acid is 12.10 g, $[a]_D^{25} - 11.3°$ (c=1, water). The product could be reused for resolution.

Racemization of optically active
p-hydroxyphenylglycine-o-toluenesulfonic acid

A mixture of L-p-hydroxyphenylglycine-o-toluenesulfonic acid(4.00 g) and water (4 ml) is heated at 140° C. for 12 hr in a sealed tube. The rate of racemization is as follows: 4 hours, 74.3%; 8 hours, 93.0%; 10 hours, 95.3%; 12 hours, 96.3%. The reaction mixture is cooled to 5° C. The resulting precipitates and the second crop obtained by concentration are collected, washed with cold water, and dried. The total yield of DL-p-hydroxyphenylglycine-o-toluenesulfonic acid is 3.4 g (85.0%), $[a]_D^{25} - 1.8°$ (c=1, water). Anal. Found: C, 53.06; H, 5.08; N,4.11. The product itself could be reused for the resolution step.

REFERENCE EXAMPLE 3

This example demonstrates the optical resolution of D-hydroxyphenylglycine according to the method described in Hongo, et al, "Asymmetric Transformation of DL-p-Hydroxyphenylglycine by a Combination of Preferential Crystallization and Simultaneous Racemization of the o-Toluenesulfonate", Bull. Chem. Soc. Japan, 58, 433-436 (1985) which is incorporated herein by reference. Optically active and racemic hydroxyphenylglycine is used. o-toluenesulfonic acid, salicylaldehyde, and other chemicals are obtained from Tokyo Kasei Kogyo Co., Ltd. Optically active and racemic hydroxyphenylglycine-o-toluenesulfonic acid are prepared in a manner described in the above example. All samples are dried overnight in vacuo at 40° C. Optical rotation is measured with a Perkin-Elmer 141 automatic polarimeter. The water content of samples is determined by the Karl-Fischer's method.

Racemization of
L-hydroxyphenylglycine-o-toluenesulfonic acid

A mixture of L-hydroxyphenylglycine-o-toluenesulfonic acid (50 mg), DL-hydroxyphenylglycine (5 mg), salicylaldehyde (3 ul), and acetic acid containing 5% water (5 ml) is heated in a sealed tube at 100° C. for 1 hour or 3 hours. After the reaction mixture is diluted with 1 M hydrochloric acid (5 ml (1M=1 mol dm$^{-3}$)), the optical rotation is measured. The racemization degree is calculated in the same way as described in the previous example. The effect of DL-hydroxyphenylglycine or salicylaldehyde in acetic acid containing water and the effect of the reaction temperature are noted.

Crystallization of DL-hydroxyphenylglycine·o-Toluenesulfonic acid from Racemizing Solution A mixture of DL-hydroxyphenylglycine·o-toluenesulfonic acid (3.8 g), DL-hydroxyphenylglycine (0.2 g), and salicylaldehyde (0.25 ml) is dissolved in acetic acid (20 ml) containing 5% water, under reflux and maintained at 100° C. The solution is seeded with finely pulverized crystals of DL-hydroxyphenylglycine·o-toluenesulfonic acid (10 mg) and stirred for 5 h at the same temperature. The precipitated crystals are quickly separated by filtration, washed with a small amount of acetic acid, and dried to give DL-hydroxyphenylglycine·o-toluenesulfonic acid (0.92 g) crystallized from racemizing solution. The melting point (213°–215° C.,dec) and IR-spectrum of the DL-hydroxyphenylglycine·o-toluenesulfonic acid are identical with those of racemic mixture of DL-hydroxyphenylglycine·o-toluenesulfonic acid shown in the previous example.

Stability of Crystalline D-hydroxyphenylglycine·o-Toluenesulfonic acid under Conditions for Racemization A mixture of DL-hydroxyphenylglycine·o-toluenesulfonic acid (1.0 g), DL-hydroxyphenylglycine (40 mg), and salicylaldehyde (50 mg) is dissolved in acetic acid containing 2% water under reflux to prepare a solution saturated with DL-hydroxyphenylglycine·o-toluenesulfonic acid at 100° C. To the saturated solution maintained at 100° C., crystals of D-hydroxyphenylglycine·o-toluenesulfonic acid (2.0 g) are added. The heterogeneous reaction mixture is stirred for 5 hours at the same temperature. The insoluble crystals are quickly separated by filtration, washed with a small amount of acetic acid, and dried. The insoluble crystals prove to be optically pure D-hydroxyphenylglycine·o-toluenesulfonic acid (1.9 g), $[a]_D^{25} -66.6°$ (c=1,water).

Asymmetric Transformation

Batch Transformation: A mixture of DL-hydroxyphenylglycine·o-toluenesulfonic acid (3.8 g), DL-hydroxyphenylglycine (0.2 g), salicylaldehyde (0.25 ml) and acetic acid (20 ml) containing 5% water is heated under reflux until a complete solution occurs and is maintained at 100° C. The supersaturated solution is seeded with finely pulverized crystals of D-hydroxyphenylglycine·o-toluenesulfonic acid (0.2 g) and stirred for 2 hours at the same temperature. The precipitated crystals are quickly separated by filtration, washed with a small amount of acetic acid, and dried to give D-hydroxyphenylglycine·o-toluenesulfonic acid (0.85 g), $[a]_D^{25} -66.6°$ (c=1, water), optical purity 100%. Subtracting 0.2 g of seeded D-hydroxyphenylglycine·o-toluenesulfonic acid, 0.65 g of pure D-hydroxyphenylglycine·o-toluenesulfonic acid is obtained. After the separation of D-hydroxyphenylglycine·o-toluenesulfonic acid, the filtrate is stirred at 20° C. for 2 hours and the precipitated crystals are collected by filtration to give DL-hydroxyphenylglycine·o-toluenesulfonic acid (2.66 g), $[a]_D^{25} +0.6°$ (c=1, water). The mother liquor does not show any optical rotation. Therefore, the whole reaction mixture becomes 17.1% enantiomeric excess.

Continuous Transformation

A mixture of DL-hydroxyphenylglycine·o-toluenesulfonic acid(19.0 g) and aqueous 95% (v/v) acetic acid (100 ml) in a three-necked flask fitted with a mechanical stirrer and a condenser is heated under reflux until complete solution occurs. Then the flask is placed in an oil bath controlled at 100° C. Salicylaldehyde (1.24 ml) is added to the solution and DL-hydroxyphenylglycine (51.0 g) is suspended therein. After 20 minutes, into the heterogeneous reaction mixture are added under stirring finely pulverized crystals of D-hydroxyphenylglycine·o-toluenesulfonic acid (2.0 g) as seed crystals. To this is poured a solution consisting of o-toluenesulfonic acid dihydrate (62.5 g) and acetic anhydride (62.5 ml) at the rate of 5.0 ml/h by a Micro Feeder JP-W (Furue Science Co., Ltd.). At 5 hours and 20 hours after the addition of the seed crystals, 1.3 ml and 0.7 ml of salicylaldehyde are added to the mixture, respectively. The mixture is stirred at the same temperature for a total of 30 hours. The precipitated crystals are quickly collected by filtration, washed with a small amount of acetic acid, and dried to give D-hydroxyphenylglycine·o-toluenesulfonic acid (82.8 g), $[a]_D^{25} -64.9°$ (c=1, water), optical purity 97.4%. After the separation of D-hydroxyphenylglycine·o-toluenesulfonic acid, the filtrate is stirred for 2 hours at room temperature and the precipitated crystals are collected by filtration to recover DL-hydroxyphenylglycine·o-toluenesulfonic acid (18.2 g), $[a]_D^{25} 0.0°$ (c=1, water). The filtrate does not show any optical rotation. The change in the composition of both enantiomers by the reaction is noted.

Preparation of D-hydroxyphenylglycine

The D-hydroxyphenylglycine·o-toluenesulfonic acid (82.0 g), obtained above is dissolved in water (230 ml) at an elevated temperature and is treated with charcoal. The solution is adjusted to PH 6 with 5 M sodium hydroxide and allowed to stand in a refrigerator overnight. The resulting precipitates are collected, washed with water, and dried to give D-hydroxyphenylglycine (34.0 g), $[a]_D^{25} -158.2°$ (c=1, M-HCl).

Reference Example 4

D-hydroxyphenylglycine may be resolved as follows according to U.S. Pat. No. 4,415,504, which is incorporated herein by reference.

(1) DL-hydroxyphenylglycine HCL (10.0 g) is reacted with (+)-phenylethanesulfate $NH_4$ (9.98 g) in water (10 ml) to form two diastereomers of DL-hydroxyphenylglycine (+)-phenylethanesulfate. DL-hydroxyphenylglycine (0.82 g) is added to the reaction mixture and the mixture is heated in an autoclave at 140° C. for 12 hours. After completion of the reaction, 50% aqueous solution of (+)-phenylethanesulfate (1.8 g) and water (10 ml) are added to the reaction mixture and the mixture is stirred at room temperature for 1 hour. The crystals thus formed are filtered off and dried to give D-hydroxyphenylglycine (+)-phenylethanesulfate (17.73 g)·$[a]_D^{25} -76.5°$ (c=1, $CH_3OH$), Optical purity 97.3%.

(2) Methanol (44 ml) is added to D-hydroxyphenylglycine (+)-phenylethanesulfate prepared in the above (1) (14.5 g) and an aqueous sodium hydroxide solution is added to the mixture with stirring to adjust pH to 6. The mixture is stirred at room temperature for 2 hours and filtered to give D-hydroxyphenylglycine (6.5 g)·$[a]_D^{25} -158.0°$ (c=1,1 N HCl). Optical purity 99.8%.

REFERENCE EXAMPLE 5

According to U.S. Pat. No. 4,094,741, DL-5-(4-hydroxyphenyl)hydantoin may be converted to D-(4-hydroxyphenyl)glycine as follows.

A liquid medium is prepared containing the following components.

| | |
|---|---|
| Meat extract | 0.5% |
| Yeast extract | 0.5% |
| Peptone | 1.0% |
| NaCl | 0.15% |

100 ml portions of this medium are poured into 500 ml shaking flasks and are steam sterilized at 120° C. for 10 minutes. To each flask is added 300 mg of sterilized DL-5-(2-methylthioethyl)hydantoin under sterile conditions. The thus obtained mixtures are employed as culture media. Each of the following microorganisms, which are previously cultured on an agar bouillon slant at 33° C. for 24 hours, is inoculated into each culture medium and is cultured at 33° C. for 22 hours with shaking.

TABLE

| Strain | N-carbamoyl-2-(4-hydroxy-phenyl glycine mg/m | Conversion (mol %) | Amount of obtained cyclohexyl amine salt of N-carbamoyl-2-(4-hydroxyphenyl)-glycine (mg) |
|---|---|---|---|
| Pseudomonas Striata IFO 12996* | 4.5 | 82 | 655 |
| Corynebacterium sepedonicum IFO 3306* | 3.0 | 55 | 491 |
| Aerobacter cloacae IAM 1221* | 1.5 | 27 | 249 |
| Agrobacterium rhizogenes IFO 13259* | 0.9 | 16 | 123 |
| Control | 0.0 | 0 | — |

*Catalog number of strains deposited at:
IFO-Institute for Fermentation, Osaka, Japan
IAM-Institute for Applied Microbiology, Univ. of Tokyo, Japan Cells are separated from each cultured broth and washed with a 0.9% saline water solution. The cells are collected again by centrifugation and then suspended into 33 ml of 0.9% saline water. Each of the thus obtained suspensions is employed as a component of the mixture described below.

Mixture Components (1) 500 mg of DL-5-(4-hydroxyphenyl)hydantoin
(2) 67 ml of 0.1 M NH$_4$Cl-NH$_4$OH buffer solution of pH 9.5
(3) 33 ml of cell suspension The hydrolysis reaction of DL-5-(4-hydroxyphenyl)hydantoin is carried out in a 300 ml ground stopper Erlenmeyer flask at 31° C. for 40 hours with mild shaking, respectively. During the reaction, the pH of the reaction mixture is maintained at 9.5 with 2N KOH. After completion of the reaction, the produced N-carbamoyl-2-(4-hydroxyphenyl)glycine is colorimetrically determined. After completion of the reaction, the reaction mixture is centrifuged and 2 ml of the supernatant solution is taken out. The supernatant solution is color-developed with 0.5 ml of a 5% solution of p-dimethylaminobenzaldehyde in 2N hydrochloric acid. The amount of N-carbamoyl-2-(4-hydroxyphenyl)glycine is colorimetrically determined by measuring the absorbance at 420 nm. The amounts of N-carbamoyl-2-(4-hydroxyphenyl)glycine produced in the reaction mixtures and the conversions from DL-5-(4-hydroxyphenyl)hydantoin are shown in the above Table.

The supernatent solution obtained by centrifuging the reaction mixture is lyophilized, and the residue is extracted with ethanol. After removing insoluble materials by filtration, to the ethanol solution is added ethyl acetate in the weight ration of ethyl acetate to ethanol of 2:1, and further added about 1.5 equivalents of dicyclohexylamine to give a white precipitate of dicyclohexylamine salt of N-carbamoyl-2-(4-hydroxyphenyl)glycine. The white precipitate is taken out and caused to react with 1.1 equivalents of sodium nitrite in an aqueous medium under acidic conditions with hydrochloric acid at room temperature for 1 hour. Then the resulting reaction mixture is passed through a column of strongly acidic cation exchange resin of H-type (commercially available as Amerlite IR-120B from Rohm & Haas) to adsorb the produced 2-(4-hydroxyphenyl)glycine on the resin. After eluting with 1.5 NH$_4$OH, crystalline 2-(4-hydroxyphenyl)glycine is isolated by concentrating the elute under reduced pressure. These procedures are repeated on each reaction mixture. The infrared spectra and Rf values by silica gel thin layer chromatography (solvent: n-butanol/acetic acid/water=4/1/1) of the thus obtained crystals agree with those of an authentic sample, and also the found data of the elementary analysis agree with the calculated value. Further, the specific rotary power of each crystal falls within the range of $[a]_D^{20} = -161.8°$ to $[a]_D^{20} = -158.5°$ (c=0.5, 1N HCl) and approximately agree with the value for D-(-)-2-(4-hydroxyphenyl)glycine, $[a]_D^{24} = -159.1°$ (c=1, 1N HCl) described in Japanese disclosure 56946/1974. It is confirmed that the described reaction products are D-(-)-2-(4-hydroxyphenyl)glycine of high purity.

REFERENCE EXAMPLE 6

According to U.S. Pat. No. 4,094,741, DL-5-(4-hydroxyphenyl)hydantoin may be converted to D-(-)-N-carbamoyl-2-(4-hydroxyphenyl)glycine as follows.

A culture medium of pH 7.0 containing the following components is prepared, and 90 ml thereof is placed in a 500 ml shaking flask and is steam sterilized at 120° C. for 10 minutes.

| Medium Components | |
|---|---|
| Meat extract | 2.0% |
| Glycerol | 1.0% |
| Hydantoin | 0.1% |

To the flask is add the cultured broth obtained previously by culturing Pseudomonas striata IFO 12996 in 10 ml of the same liquid medium as above in a test tube at 33° C. for 24 hours, and the culture is carried out at 33° C. for 20 hours with shaking. Cells are separated from the resulting cultured broth by centrifugation and washing with 100 ml of 0.9% saline water. The cells are collected again by centrifugation to give 2.62 g of the intact cells. The thus obtained intact cells are suspended into 10.4 ml of 0.9% saline water and thereto are added 1.0 g of acrylamide and 105 mg of N,N'-methylenebis(acrylamide) and further added 1.3 ml of a 5% aqueous solution of dimethylaminopropionitrile and 1.3 ml of a 2.4% aqueous solution of ammonium persulfate. The resulting mixture is shaken. The mixture gels after several minutes. The mixture is further maintained at 36° C. for 30 minutes to complete the reaction. To the obtained gel containing cells is added a small amount of 0.9% saline water and the gel is crushed in a mortar and the resulting granules are washed with 0.9% saline water to give 2.5 g of immobilized cells. A 200 ml four neck flask equipped with a stirrer is charged with 2.0 g of DL-5-(4-hydroxyphenyl)hydantoin and 80 ml of deionized water. To this flask is added a 2N solution of NaOH to adjust the liquid to pH 7.0 and further added are the immobilized cells suspended in 110 ml of deionized water. After adjusting the mixture to pH 8.7, the reaction is carried out at 36° C. with mild agitation. During the reaction, the pH of the reaction mixture is maintained at pH 8.7 with a 2N aqueous solution of NaOH. The reaction is approximately completed in 15 hours. At that time, the total volume of the reaction mixture is 200 ml. The amount of D-(-)-N-carbamoyl-2-(4-hydroxyphenyl)glycine produced in the reaction mixture is 10.4 mg/ml and the conversion from DL-5-(4-hydroxyphenyl)hydantoin is 98% by mole.

While specific reactants, reaction conditions, and equipment are described above to enable one skilled in the art to practice the invention, one skilled in the art will be able to make modifications and adjustments which are obvious extensions of the present invention. Such obvious extensions of or equivalents to the present invention are intended to be within the scope of the present invention as demonstrated by the claims which follow.

What is claimed is:

1. A method for producing an hydroxyaromatic ketoacetal which comprises the steps of:
   a) contacting an hydroxymethylketone with a source of H+, a source of NO+ and a primary or secondary alcohol; and
   b) reacting the mixture created upon said contacting to produce an hydroxyaromatic ketoacetal.

2. The method of claim 1, wherein said hydroxymethylketone is p-hydroxyacetophenone.

3. The method of claim 1, wherein said hydroxyaromatic ketoacetal is the dialkyl acetal of 4-hydroxyphenylketoaldehyde.

4. A method of producing an hydroxyaromatic ketoaldehyde comprising the steps of claim 1 and an additional step:
   c) hydrolyzing said hydroxyaromatic ketoacetal to form an hydroxyaromatic ketoaldehyde.

5. The method of claim 4, wherein said hydroxymethylketone is p-hydroxyacetophenone.

6. The method of claim 5, wherein said hydroxyaromatic ketoacetal is the dialkyl acetal of 4-hydroxyphenylketoaldehyde.

7. The method of claim 1, claim 2, claim 3, claim 4, or claim 5, wherein said source of NO+ comprises a reactant NO+X, wherein X is selected from the group consisting of halogen, sulfite, sulfate, phosphite, and phosphate.

8. The method of claim 7, wherein X is halogen.

9. The method of claim 8, wherein X is chlorine.

10. The method of claim 1, claim 2, claim 3, claim 4, or claim 5, wherein said source of NO+ comprises a $C_1$-$C_{10}$ alkyl nitrite.

11. A method for producing 5-(4'-hydroxyphenyl)hydantoin which comprises:
   a) contacting 4-hydroxyacetophenone, a source of H+, a source of NO+, and a primary or secondary alcohol to form an intermediate; and then
   b) reacting said intermediate with urea, water and concentrated mineral acid to thereby produce 5-(4'-hydroxyphenyl)hydantoin.

12. The method of claim 11, wherein said source of NO+ comprises a $C_1$ to $C_{10}$ alkyl nitrite.

13. The method of claim 12, wherein said source of H+ is hydrogen chloride.

14. The method of claim 11, wherein said source of NO+ comprises a reactant NO+X, wherein X is selected from the group consisting of halogen, sulfite, sulfate, phosphite and phosphate.

15. The method of claim 14, wherein said NOX is NOCl.

16. The method of claim 11, wherein said mineral acid is hydrochloric acid.

17. The method of claim 12, wherein the $C_1$ to $C_{10}$ alkyl nitrite present in the composition in an amount of from about 1 to about 3 mole equivalents of the amount of 4-hydroxyacetophenone.

18. The method of claim 11, wherein the primary or secondary alcohol is present in a large excess of that amount required for the reaction to take place.

19. The method of claim 11, wherein the primary or secondary alcohol is present in an amount of from about 2 to about 10 times the weight of the 4-hydroxyacetophenone.

20. The method of claim 16, wherein the hydrogen chloride is present in at least a catalytic amount.

21. The method of claim 20, wherein the hydrogen chloride is present in an amount of from about 0.1 to about 6 mole equivalents of the amount of 4-hydroxyacetophenone.

22. The method of claim 11, wherein step a) is conducted for a time period ranging from about 1 hour to about 24 hours.

23. The method of claim 11, wherein the urea present in step b) in an amount of from about 1 to about 4 mole equivalents of the amount of 4-hydroxyacetophenone.

24. The method of claim 11, wherein the water in step b) is present in a large excess of that amount required for the reaction to take place.

25. The method of claim 24, wherein the water is present in an amount of from about 0.1 to about 3 times the weight of the alcohol.

26. The method of claim 16, wherein the concentrated hydrochloric acid is present in a least a catalytic amount.

27. The method of claim 26, wherein the concentrated hydrochloric acid present in the composition in an amount of from about 0.1 to about 8 mole equivalents of the amount of 4-hydroxyacetophenone.

28. The method of claim 11, wherein the first step is conducted at a temperature of from about −10° C. to about 50° C. for from about 0.5 hour to about 24 hours.

29. A method for producing p-hydroxyphenylglycine which comprises:
   a) contacting 4-hydroxyacetophenone, a source of H+, a source of NO+, and a primary or secondary alcohol to form an intermediate; and then
   b) reacting said intermediate with urea, water, and concentrated mineral acid to thereby produce 5-(4'-hydroxyphenyl)hydantoin; and then
   (c) hydrolyzing 5-(4'-hydroxyphenyl)hydantoin to thereby produce p-hydroxyphenylglycine.

30. The method of claim 29, wherein the source of NO+ is a $C_1$ to $C_{10}$ alkyl nitrite present in the composition in an amount of from about 1 to about 3 mole equivalents of the amount of 4-hydroxyacetophenone.

31. The method of claim 29, wherein the primary or secondary alcohol is present in a large excess of that amount required for the reaction to take place.

32. The method of claim 31, wherein the primary or secondary alcohol is present in an amount of from about 2 to about 10 times the weight of the 4-hydroxyacetophenone.

33. The method of claim 29, wherein the mineral acid is hydrogen chloride which is present in at least a catalytic amount.

34. The method of claim 33, wherein the hydrochloric acid is present in an amount of from about 0.1 to about 6 mole equivalents of the amount of 4-hydroxyacetophenone.

35. The method of claim 29, wherein the step a) is conducted for from about 1 hour to about 24 hours.

36. The method of claim 29, wherein the urea is present in an amount of from about 1 to about 4 mole equivalents of the amount of 4-hydroxyacetophenone.

37. The method of claim 29, wherein the water in step b) is present in a large excess of that amount required for the reaction to take place.

38. The method of claim 37, wherein the water in step b) is present in an amount of from about 0.1 to about 3 times the weight of the alcohol.

39. The method of claim 33, wherein the concentrated hydrochloric acid present in the composition in an amount of from about 0.1 to about 8 mole equivalents of the amount of 4-hydroxyacetophenone.

40. The method of claim 29, wherein the first step is conducted at a temperature of from about $-10°$ C. to about 50° C. for from about 0.5 hour to about 24 hours.

41. A method for producing D-p-hydroxyphenylglycine which comprises:
    a) contacting 4-hydroxyacetophenone, a source of H+, a source of NO+, and primary or secondary alcohol to form an intermediate; and then
    b) reacting said intermediate with urea, water and concentrated mineral acid to thereby produce 5-(4'-hydroxyphenyl)hydantoin; and then
    c) hydrolyzing 5-(4'-hydroxyphenyl)hydantoin to thereby produce p-hydroxyphenylglycine; and then
    d) optically resolving p-hydroxyphenylglycine to produce D-p-hydroxyphenylglycine.

42. The method of claim 41, wherein the source of NO+ is a $C_1$ to $C_{10}$ alkyl nitrite.

43. The method of claim 41, wherein the mineral acid used in step b) is hydrochloric acid.

44. The method of claim 41, wherein the optical resolution is conducted with D-bromocamphor sulfonic acid, or an aromatic sulfonate.

45. The method of claim 41, wherein the optical resolution is conducted by reacting DL-hydroxyphenylglycine and D-bromocamphor sulfonic acid monohydrate to produce D-p-hydroxyphenylglycine·D-bromocamphor sulfonic acid, then dissolving, concentrating and crystallizing D-p-hydroxyphenylglycine·D-bromocamphor sulfonic to produce precipitated crystals of D-p-hydroxyphenylglycine.

46. The method of claim 41, wherein the optical resolution is conducted by forming an aromatic sulfonate of p-hydroxyphenylglycine, optically resolving and purifying the aromatic sulfonate by crystallization, and then neutralizing with an alkali or ion exchange resin to give D-p-hydroxyphenylglycine.

47. The method of claim 41, wherein the resolution is conducted with o-toluene sulfonic acid.

48. The method of claim 41, wherein the optical resolution is conducted by reacting DL-hydroxyphenylglycine with HCl to form DL-hydroxyphenylglycine·HCl, reacting DL-hydroxyphenylglycine·HCl with a (+)-phenylethanesulfate to form DL-hydroxyphenylglycine (+)-phenylethanesulfate, then heating and crystallizing to produce D-hydroxyphenylglycine (+)-phenylethanesulfate and reacting with methanol and an aqueous sodium hydroxide solution to give D-hydroxyphenylglycine.

49. A method for producing D-p-hydroxyphenylglycine which comprises:
    a) contacting 4-hydroxyacetophenone, a source of H+, a source of NO+, and a primary or secondary alcohol to form an intermediate; and then
    b) reacting said intermediate with urea, water and concentrated mineral acid to thereby produce 5-(4'-hydroxyphenyl)hydantoin; and then
    c) enzymatically hydrolyzing 5-(4'-hydroxyphenyl)hydantoin to thereby form D-5-(4'-hydroxyphenyl)hydantoic acid, and then
    d) decarbamoylating D-5-(4'-hydroxyphenyl)hydantoic acid to thereby form D-p-hydroxyphenylglycine.

50. The method of claim 49, wherein the source of NO+ is a $C_1$ to $C_{10}$ alkyl nitrite.

51. The method of claim 49, wherein the mineral acid used in step b) is hydrochloric acid.

52. The method of claim 49, wherein the hydrolysis of racemic p-hydroxyphenyl hydantoin to produce N-carbamoyl-D-p-hydroxyphenylglycine is conducted with microbial hydantoinase in a cultured broth.

53. The method of claim 52, wherein the pH is maintained during the hydrolysis reaction with an alkaline solution.

54. The method of claim 52, wherein the hydrolysis reaction is conducted under an inert gas.

55. The method of claim 52, wherein the N-carbamoyl-D-p-hydroxyphenylglycine is decarbamoylized with nitrous acid or a water soluble salt of nitrous acid under acidic conditions to produce D-p-hydroxyphenylglycine.

56. The method of claim 55, wherein the decarbamoylation is carried out by reacting N-carbamoyl-D-p-hydroxyphenylglycine with an approximately equimolar amount of nitrous acid in an aqueous medium in the presence of a strong mineral acid.

57. The method of claim 55, wherein the strong mineral acid is sulfuric or hydrochloric acid.

58. The method of claim 55, wherein the water soluble salt of nitrous acid is sodium nitrite or potassium nitrite.

59. The method of claim 55, wherein the decarbamoylation reaction temperature is maintained at about 20° C. or below.

* * * * *